United States Patent
Willbold et al.

(10) Patent No.: US 10,746,747 B2
(45) Date of Patent: Aug. 18, 2020

(54) METHOD FOR QUANTITATIVE CHARACTERIZATION OF SUBSTANCES WITH REGARD TO THEIR PROPERTIES OF BINDING TO AMYLOID-β (Aβ) CONFORMERS

(71) Applicant: FORSCHUNGSZENTRUM JUELICH GMBH, Juelich (DE)

(72) Inventors: Dieter Willbold, Juelich (DE); Julian Glueck, Meerbusch (DE); Daniel Frenzel, Aachen (DE); Luitgard Nagel-Steger, Langenfeld (DE); Oleksandr Brener, Duesseldorf (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 0 days.

(21) Appl. No.: 14/902,760

(22) PCT Filed: Jun. 25, 2014

(86) PCT No.: PCT/DE2014/000320
§ 371 (c)(1),
(2) Date: Jan. 4, 2016

(87) PCT Pub. No.: WO2015/003675
PCT Pub. Date: Jan. 15, 2015

(65) Prior Publication Data
US 2017/0234890 A1    Aug. 17, 2017

(30) Foreign Application Priority Data
Jul. 12, 2013    (DE) .......................... 10 2013 011 636

(51) Int. Cl.
*G01N 33/68* (2006.01)
*G01N 33/543* (2006.01)

(52) U.S. Cl.
CPC ...  *G01N 33/6896* (2013.01); *G01N 33/54366* (2013.01); *G01N 33/54373* (2013.01); *G01N 2333/4709* (2013.01); *G01N 2500/20* (2013.01)

(58) Field of Classification Search
CPC ....... G01N 33/6896; G01N 2333/4709; G01N 2500/20; G01N 33/54366; G01N 33/54373
See application file for complete search history.

(56) References Cited

U.S. PATENT DOCUMENTS

2003/0203403 A1    10/2003    Peach et al.

FOREIGN PATENT DOCUMENTS

WO    WO-2014067505 A2 *    5/2014    ............... C07K 7/08

OTHER PUBLICATIONS

Sehlin et al. Large Aggregates Are the Major Soluble Aβ Species in AD Brain Fractionated with Density Gradient Ultracentrifugation. PLoS One. 2012;7(2):e32014. doi: 10.1371/journal.pone.0032014. Epub Feb. 15, 2012.*
Silke Dornieden et al: "Characterization of a Single-Chain Variable Fragment Recognizing a Linear Epitope of A{beta;} a Biotechnical Tool for Studies on Alzheimer's Disease?", PLOS One, vol. 8, No. 3, Mar. 1, 2013 (Mar. 1, 2013), p. e59820, XP55142153, ISSN: 1932-6203, coi: 10.1371/journal.pone.0059820 (S 3-4, uebergreifender Abs: S 6-7, uebergreifender Abs; Fig. 6B).
M. Stravalaci et al: "Specific Recognition of Biologically Active Amyloid-oligomers by a New Surface Plasmon Resonance-based Immunoassay and an in Vivo Assay in Caenorhabditis elegem", Journal of Biological Chemistry, vol. 287, No. 33, Jun. 26, 2012 (Jun. 26, 2012), pp. 27796-27805, XP055142125, ISSN: 0021-9258, DOI: 10.1074/jbc.M111.334979 S 27796:27797, uebergreifender Abs.
Olubiyi O O et al: "Amyloid aggregation inhibitory mechanism of arginine-rich D-peptides", Current Medicinal Chemistry, Bentham Science Publ, NL, vol. 21, No. 12, Jan. 1, 2014 (Jan. 1, 2014), pp. 1448-1457. XP009180173, ISSN: 1875-533X p. 1451, co. 1-2; abstract.
Daniel Frenzel et al: "Immobilization of Homogeneous Monomeric, Oligomerie and Fibrillar A[beta] Species for Reliable SPR Measurements", PLOS One, vol. 9, No. 3, Mar. 3, 2014 (Mar. 3, 2014), p. e89490, XP055142127, DOI: 10.1381/journal.pone.0089490 p. 2, col. 1, paragraph 2-p. 4, col. 1, paragraph 1; figure 1.

* cited by examiner

Primary Examiner — Gregory S Emch
(74) Attorney, Agent, or Firm — Norris McLaughlin, P.A.

(57) ABSTRACT

A method for the quantitative characterization of substances with regard to their properties of binding to amyloid-β (Aβ) conformers, comprising the steps of: —fractionating a sample including various Aβ conformers; —immobilizing a biotinylated Aβ conformer of the desired fraction on the surface of a substrate having high affinity for biotin; and —deriving the binding behavior of an aggregate quality control probe to the desired Aβ conformer from the measurement signal by determining the kinetic and/or thermodynamic parameters. A device for carrying out the method.

12 Claims, 4 Drawing Sheets
Specification includes a Sequence Listing.

METHOD FOR QUANTITATIVE CHARACTERIZATION OF SUBSTANCES WITH REGARD TO THEIR PROPERTIES OF BINDING TO AMYLOID-β (Aβ) CONFORMERS

The invention relates to a method for the quantitative characterization of substances with regard to their properties of binding to amyloid-β (Aβ) conformers.

BACKGROUND OF THE INVENTION

The biotin-streptavidin coupling of ligands to a biosensor is prior art. A ligand is biotinylated and is immobilized on a sensor surface that is loaded with streptavidin. Analytes to be tested are detected by the binding to the ligands. Disadvantageously, this method requires regeneration steps which are time-consuming and disrupt the non-covalent binding of the ligand to the surface.

Dornieden et al. were able to show, by means of a ThT assay, that the antibody fragment scFv-IC16 hinders Aβ fibril formation in samples containing Aβ 1-42. The same publication described binding a synthetic Aβ 1-42 peptide via its C-terminal cysteine to the sensor surface of a CM5 sensor chip from GE Healthcare. Surface plasmon resonance was carried out in order to characterize the binding behavior of the antibody fragment scFv-IC16 to Aβ conformers. The antibody fragment scFv-IC16 was the analyte in these experiments.

No approved medicament exists for treating the cause of Alzheimer's dementia (AD). Deposits of the so-called beta-amyloid peptide (Aβ) in plaques are typically found post mortem in the brains of AD patients. Various forms of A1, for example fibrils, have been blamed for the onset and progression of AD. For the past few years, small Aβ aggregates (Aβ oligomers) in particular have been blamed as the main culprit for the onset and progression of AD. Reduction or complete elimination of Aβ oligomers would thus appear to be the most important criterion for curing or slowing AD. Aβ monomers are constantly being produced in our body and are presumably not toxic per se. There is speculation as to whether Aβ monomers agglomerate randomly depending on their concentration (which ultimately results from the rate at which they are formed and broken down in the body) and thus are increasingly more likely to form Aβ oligomers spontaneously as a person gets older. Once formed, Aβ oligomers could then multiply through a prion-like mechanism and ultimately lead to the disease. Based on these considerations, causal treatment should be aimed at completely destroying toxic Aβ oligomers, and possibly also other oligomer forms, and/or hindering the prion-like multiplication thereof.

One important point is the fact that any active ingredient has to be tested in an animal model and in clinical studies. These are very time-consuming and costly. A rapid, reliable and quantitative in vitro analysis, which permits both a screening of various potential active ingredients as well as the effect of active ingredient optimizations on the specific binding behavior for different Aβ conformers (monomers, oligomers, fibrils), would be of great advantage. In addition, a direct detection of Aβ oligomers and/or other conformers other than monomers at any desired point in time during the measurement is an important requirement for functioning as a control/quality standard.

For quantitative binding analyses of substances, surface plasmon resonance (SPR) technology is primarily used at present since this enables conclusions to be drawn about the underlying association and dissociation rates in addition to binding affinities. For interaction studies, one of the two interaction partners must be immobilized on the sensor surface. This is known as the ligand.

Due to the high susceptibility of Aβ oligomers to changes in structure, use as an analyte (injected molecule) is not advisable. For immobilizing molecules, various covalent and non-covalent strategies currently exist. One particular challenge in the case of Aβ oligomers is the high susceptibility thereof to undergoing structural changes as a result of changes in the surrounding solution conditions, which cannot be avoided in the case of covalent coupling methods. Non-covalent immobilization techniques, so-called capture methods, are the method of choice here. In this case, however, there is a need to find a successful combination of suitable Aβ oligomer preparation methods with non-covalent immobilization methods.

Nevertheless, in various current publications, there is a trend toward covalent immobilization without taking account of resulting possible structural changes in the case of immobilized Aβ oligomers.

Regeneration steps between individual analyte injections are a further source of error in SPR measurements, since these can likewise bring about structural changes.

Detection using antibodies serves as a common detection method for the successful immobilization of Aβ oligomers on sensor surfaces. Due to the bivalent nature of the antibodies, avidity effects disadvantageously occur, which do not allow for a complete dissociation of the molecules in a reasonable length of time, without the addition of additives and again require regeneration steps.

Due to the described high-susceptibility to structural changes as a result of changing solution conditions which are necessary due to conventional immobilization protocols, regeneration steps between individual analyte injections and antibody control injections, measurement artefacts cannot be avoided in interaction studies using oligomeric Aβ forms. This harbors the risk that measurement data obtained are possibly highly subject to errors.

The problem addressed by the invention is that of providing a method for the quantitative characterization of substances with regard to their properties of binding to various amyloid-β (Aβ) conformers. This would permit screening and the optimization of substances to be tested, for example against Alzheimer's dementia (AD). Another problem addressed by the invention is that of providing a device for carrying out the method.

DESCRIPTION OF THE PREFERRED EMBODIMENTS

Figure 1:
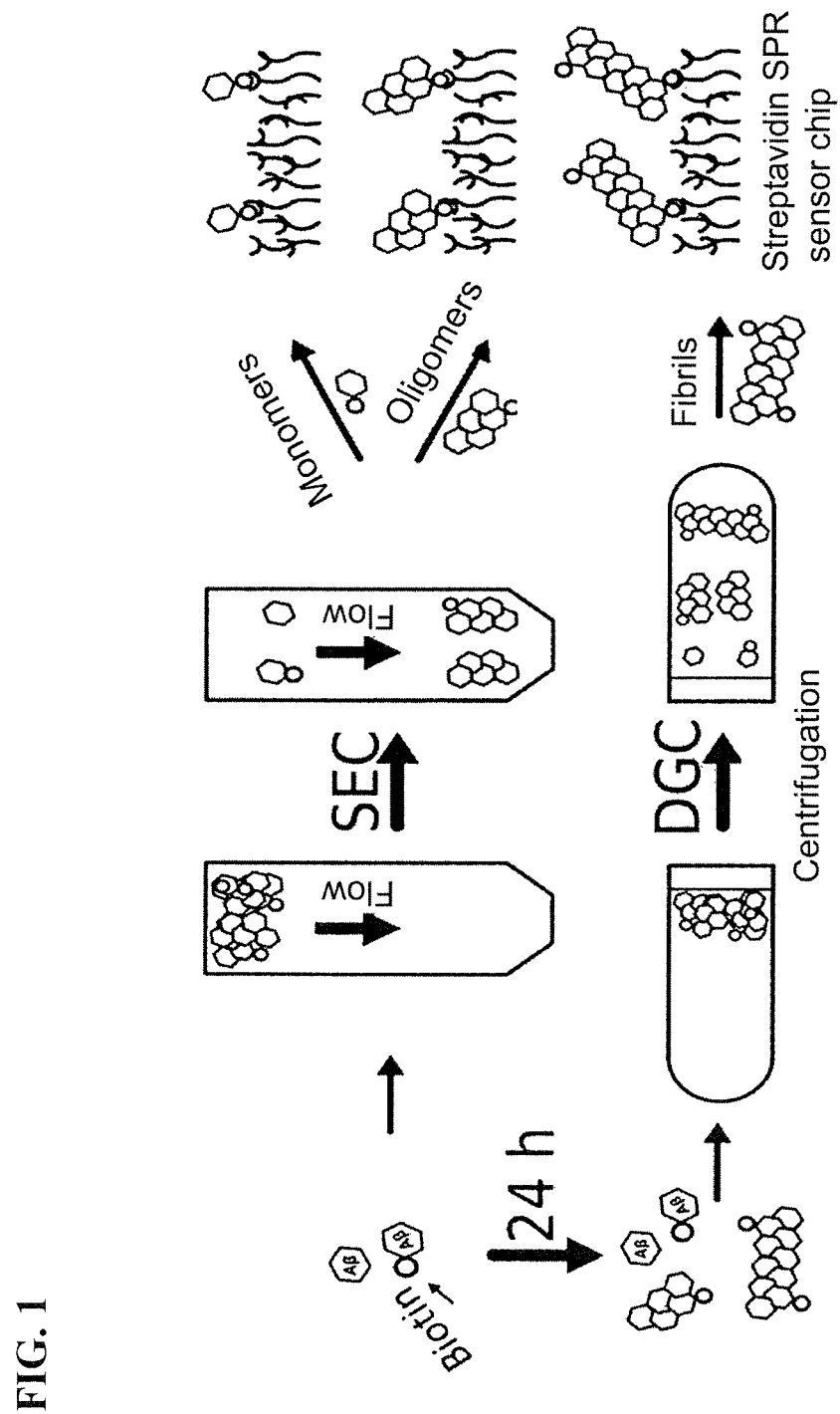
FIG. 1 shows a flowchart of the sample preparation of monomeric, oligomeric and fibrillar Aβ(1-42) forms, with subsequent immobilization on SPR sensor surfaces.

A method is claimed for the quantitative characterization of a substance with regard to its properties of binding to amyloid-β (Aβ) conformers, comprising the steps of:

fractionating a sample including the various Aβ conformers;

immobilizing a biotinylated AB conformer of the desired fraction on the surface of a substrate having high affinity for biotin; and deriving the binding behavior of an aggregate quality control probe to the desired Aβ conformer from the measurement signal by determining the kinetic and/or thermodynamic parameters.

By using an aggregate quality control probe instead of a test substance, the quality of the immobilized aggregates can advantageously be checked at any point in time during the experiments.

A sample including monomeric Aβ and monomeric N-terminally biotinylated Aβ or exclusively monomeric N-terminally biotinylated Aβ may be prepared and incubated so that various conformers of Aβ are formed in the sample through aggregation.

For in vitro analyses, the sample can preferably be produced from lyophilized starting components. To this end, the incubation of the Aβ molecules can take place in HFIP, which is subsequently evaporated off again. The Aβ molecule of choice, for example Aβ 1-42, in the desired mixing ratio of N-terminally biotinylated to non-biotinylated molecules is then taken up in buffer.

All the Aβ molecules used to produce the sample may be in N-terminally biotinylated form. In this case, the binding of space-filling ligands to continuous epitopes, which contain the N-terminal amino acid residue, may be restricted. Discontinuous epitopes are created from the primary structures of the Aβ molecules by aggregation. This detection of the binding of molecules (aggregate quality control probe and/or substance to be tested) can be the focus of the method according to the invention. However, mixtures of N-terminally biotinylated and non-biotinylated Aβ molecules can also be used to produce the sample, and can be set in a desired ratio to one another at the outset. The ratio of N-terminally biotinylated to non-biotinylated molecules should preferably be less than 1:1 down to as little as 1:50. Depending on the species to be immobilized, it is also conceivable to use a lower ratio of N-terminally biotinylated to non-biotinylated molecules, such as 1:100 for example.

The N-terminally biotinylated molecules in an aggregate also ensure the immobilization of the non-biotinylated Aβ molecules in the same aggregate to a substrate surface.

In this case, due to the downstream quantitative method, the binding of aggregate quality control probe and/or substance to be tested to the exposed N-terminal primary structures of Aβ molecules is also possible. This detection of the binding of molecules can likewise be the focus of the method.

With particular advantage, a ratio of N-terminally biotinylated to non-biotinylated AP molecules of less than or equal to 1:10 to 1:40 is used.

In in vitro studies, the desired ratio can be mixed from synthetically provided N-terminally biotinylated and non-biotinylated Aβ molecules from a supplier after each being taken up in HFIP. As a result, advantageously all the molecule mixtures used during the experiment are already biotinylated in the desired ratio prior to the start of aggregation.

In order to permit the immobilization of oligomeric Aβ forms, during which no risks of structural changes are introduced, N-terminally biotinylated Aβ peptides are co-incubated with Aβ in a ratio of less than or equal to 1:10.

By virtue of this step, advantageously, a targeted capture immobilization is possible, in particular of oligomeric and higher Aβ forms using sensor surfaces loaded with streptavidin or avidin, without additionally required changes to the solution conditions.

The co-incubated peptides of N-terminally biotinylated and non-biotinylated molecules of a fraction are to this end immobilized on the streptavidin-loaded (avidin-loaded) surface of the substrate. The high streptavidin-biotin (or avidin-biotin) affinity of the two binding partners is thus used as the immobilization mechanism.

After incubation, the sample includes the various possible conformers of Aβ, such as for example monomers, oligomers, fibrils and higher conformation structures of Aβ.

The method is particularly suitable for carrying out quantitative analyses on the Aβ 1-42 conformers that have a high tendency to aggregate, in particular on the Aβ 1-42 oligomers. The claimed method has been developed for this in particular. Of course, however, other Aβ species, such as Aβ 1-40 for example, are also possible as the immobilized ligand of the method. The use of mixtures of multiple different Aβ species, such as for example Aβ 1-40, Aβ 1-42 and pyroglutamyl-Aβ 3-40, is also possible.

The sample including the various Aβ conformers is then fractionated. In each fraction, depending on the fractionation step, different conformers are enriched and can be precisely determined.

The term "precisely determined" encompasses a calibration step during the fractionation using molecules of known type and behavior. After the fractionation, only one particular type of conformer of Aβ is present in each fraction, for example oligomers or fibrils and so on.

With density gradient centrifugation as the fractionation step, the conformers are separated according to their s value or sedimentation coefficient. Molecules of different size can have an identical hydrodynamic radius but nevertheless have different s values and will therefore also be separated according to this. By way of calibration using molecules of known s value, the Aβ conformers obtained by means of density gradient centrifugation are precisely determined according to their s value.

In the case of size exclusion chromatography, on the other hand, the fractions are formed on the basis of the size of the Aβ molecules. These can consequently be assigned to the known monomers and oligomers.

Each fraction to be subsequently analyzed is thus precisely determined with regard to the Aβ conformer it contains.

In this way, with particular advantage, a quantitative analysis of specifically one particular Aβ conformer is possible. As far as the applicant is aware, this is the case for the first time in the present patent application.

In terms of fractionation, consideration is given in particular to density gradient centrifugation and size exclusion chromatography. Density gradient centrifugation has the very particular advantage that all Aβ conformers can thereby be separated from one another in a single method step. Size exclusion chromatography can be carried out if the Aβ oligomers or monomers are to be used for the quantitative analysis. On the other hand, size exclusion chromatography is unable to separate Aβ fibrils, which are insoluble in the mobile phase, from other Aβ conformers.

By using a density gradient centrifugation step prior to the immobilization, during which oligomeric or higher Aβ forms are layered onto a pre-formed density gradient and the aggregate particles contained therein are separated according to their s value by ultracentrifugation, in the course of this centrifugation different Aβ aggregates (oligomers and fibrils or amorphous aggregates) can be separated from one another and fractionated according to their sedimentation coefficient, which depends inter alia on the particle size. The fraction containing the desired Aβ conformer can then be injected directly onto a streptavidin-loaded sensor surface for immobilization purposes.

The Aβ conformer of a particular fraction, which does not include the monomer, is thus immobilized on the surface of a substrate having high affinity for biotin. As substrates, use may be made in general of all streptavidin- or avidin-coated substrates, and in particular the biosensors for surface plasmon resonance or biolayer interferometry.

In this way, precisely defined Aβ conformers are immobilized on the sensitive surface of the biosensors for biolayer interferometry and/or biosensors for surface plasmon resonance. This advantageously means that, for the first time, the biosensors for biolayer interferometry or the biosensors for surface plasmon resonance are specifically coated with one single, precisely determined conformer and not, as was customary in the prior art, with a mixture of various Aβ conformers.

The quantitative analysis then provides for adding an aggregate quality control probe, which specifically recognizes the N-terminal region of the conformer, to the immobilized Aβ conformer. In this case, with particular advantage, the binding of the aggregate quality control probe to the N-terminal biotinylated regions of the molecules is suppressed since, due to the steric occurrences of the biotin, the aggregate quality control probe provided for detection purposes cannot recognize the binding region on the N-terminal region of the molecules.

With particular advantage, therefore, the kinetics of the binding of the aggregate quality control probe to the immobilized Aβ conformer are defined. Depending on the approach with or without non-biotinylated molecules, discontinuous epitopes are also included.

This approach makes it possible to quantitatively determine the immobilization efficiency of the non-monomeric conformer from a fraction by way of the binding of the aggregate quality control probe.

The method is characterized inter alia in that an immobilization of co-incubated peptides can be monitored using an antibody fragment, such as scFv-IC16 for example, as the aggregate quality control probe. It is conceivable to use a different antibody which specifically recognizes the N-terminal regions.

In this case the detection of successful immobilization of oligomeric or multimeric Aβ conformers takes place with the aid of an antibody fragment, a so-called single chain variable fragment (scFv-IC16), which specifically recognizes the N-terminal region of Aβ. Due to the biotinylation of Aβ at the N-terminal region, binding of the scFv-IC16 is inhibited. With particular advantage, by virtue of the method according to the invention and the device for carrying out the method, a positive binding signal is nevertheless obtained with scFv-IC16 or other antibodies after the immobilization of oligomeric and other multimeric Aβ forms.

Thus, this constitutes direct detection for non-monomeric Aβ conformers, since no signal can occur in the case of monomeric N-terminally biotinylated Aβ. In addition, scFv-IC16 advantageously has dissociation behavior which permits complete dissociation after a brief waiting time. To this end, with particular advantage, the antibody fragment scFv-IC16 need only be eluted with buffer.

By virtue of the method, advantageously the maximum possible binding sites can be quantitatively determined. Since the complex consisting of bound antibody fragment scFv-IC16 on non-biotinylated Aβ is characterized by a high dissociation constant $K_D$, it is advantageously ensured that other binding partners of Aβ can thereafter be quantitatively analyzed, for example substances to be tested such as D3 or D3D3 or D7.

The method is not limited to this. Rather, all possibilities for binding of the immobilized, non-biotinylated peptides by the antibody fragment scFv-IC16 are detected and used as control for the quantitative analysis of the substance to be tested. It is possible to detect not only the possible bindings to the sensor surface according to the primary structure as a whole, but also further secondary binding possibilities which are brought about by the multimeric conformations of the disposed peptides.

A substance to be tested which is added to the immobilized conformer can be determined with regard to its kinetics of binding to the immobilized conformer. As a result, active ingredient analyses are possible.

In this case, advantageously, the binding kinetics of the substance to be tested to Aβ are also compared with the binding kinetics of the aggregate quality control probe, wherein the aggregate quality control probe and in particular an antibody fragment scFv-IC16 serves as positive control.

The results can be obtained by surface plasmon resonance or by biolayer interferometry. In the case of surface plasmon resonance, regeneration steps between individual analyte injections are circumvented by carrying out the interaction studies using the "single-cycle kinetics" measurement method. Thus, advantageously, different analyte concentrations are injected directly one after the other.

A device according to the invention for carrying out such a method is characterized in that a particular Aβ conformer, which does not include monomeric Aβ, is immobilized on a substrate surface having high affinity for biotin.

The device may be a commercially available streptavidin- or superstreptavidin- or avidin-containing biosensor for biolayer interferometry or a corresponding biosensor for surface plasmon resonance.

A substance to be tested, which is added to the peptide immobilized in this way on the substrate surface, is then precisely analyzed quantitatively, by surface plasmon resonance or by biolayer interferometry, with regard to the kinetics and thermodynamics of the binding behavior to the peptide.

In summary, the invention consists of the targeted combination of various techniques: the preparation of the Aβ conformers to be immobilized, preferably by means of size exclusion chromatography or density gradient centrifugation, the subsequent immobilization by means of biotin-streptavidin (-avidin) on a substrate surface, the specific detection of oligomeric or multimeric Aβ conformers using specific antibodies, such as scFv-IC16 for example, and the use of the single-cycle kinetics measurement method in the case of surface plasmon resonance.

The overall outlay on apparatus is low with regard to the result achieved, since all that is required is an ultracentrifuge and an instrument by which the kinetics of protein interactions can be studied, during which immobilization of molecules is necessary or possible.

The invention will be described in greater detail below, on the basis of exemplary embodiments and the appended figures, without this being intended to limit the invention in any way.

In order to ensure a homogeneous sample preparation, monomers and oligomers were separated by means of size exclusion chromatography (SEC), and fibrils were separated from other forms by means of density gradient centrifugation. The immobilization on streptavidin-loaded SPR sensor surfaces took place by using biotinylated Aβ(1-42), oligomers and fibrils being composed of a 1:10 ratio of biotinylated Aβ(1-42) to non-biotinylated Aβ(1-42).

The lyophilized samples of N-terminally biotinylated Aβ(1-42) and non-biotinylated Aβ(1-42) were each dissolved separately from one another in 100% hexafluoroisopropanol (HIFP) and incubated overnight at room temperature. The volumes required for a 1:10 ratio were then combined and the HFIP was evaporated off using a concentrator.

For the preparation of monomeric and oligomeric Aβ(1-42), the previously obtained pellet was taken up in the size exclusion chromatography buffer (50 mM sodium phosphate buffer, 150 mM NaCl, 0.6% Tween 20, pH 7.4) and briefly centrifuged for 30 seconds at 15500 g in order to sediment insoluble material.

For the preparation of fibrillar Aβ(1-42), the pellets obtained after the evaporation were dissolved in 10 mM sodium phosphate buffer pH 7.4 and incubated for 24 hours at 25° C. and at 600 rpm.

The supernatant after the centrifugation step at the end of the preparation of monomeric and oligomeric Aβ(1-42) was then applied directly to a Superdex 75 10/300 GL (GE Healthcare) column for chromatographic separation. The flow rate during the elution with size exclusion chromatography buffer was 0.8 ml/min. Monomers eluted at ~14 ml, whereas oligomers eluted at ~8 ml.

The density gradient was prepared by subsequently layering over the density gradient solution (iodixanol diluted in 10 mM sodium phosphate buffer pH 7.4) in concentrations of 50% (260 μl), 40% (260 μl), 30% (260 μl), 20% (260 μl), 10% (260 μl) and 5% (100 μl) (v/v). The samples were then pipetted onto the density gradient and centrifugation was carried out for 3 hours at 4° C. and 259000 g. A total of 14 fractions, each of 140 μl, was then removed from the density gradient from top to bottom. Monomers are found in the first fraction, oligomers are found in fractions 5 and 6, and fibrils are found typically in fractions 11-13.

Figure 2:
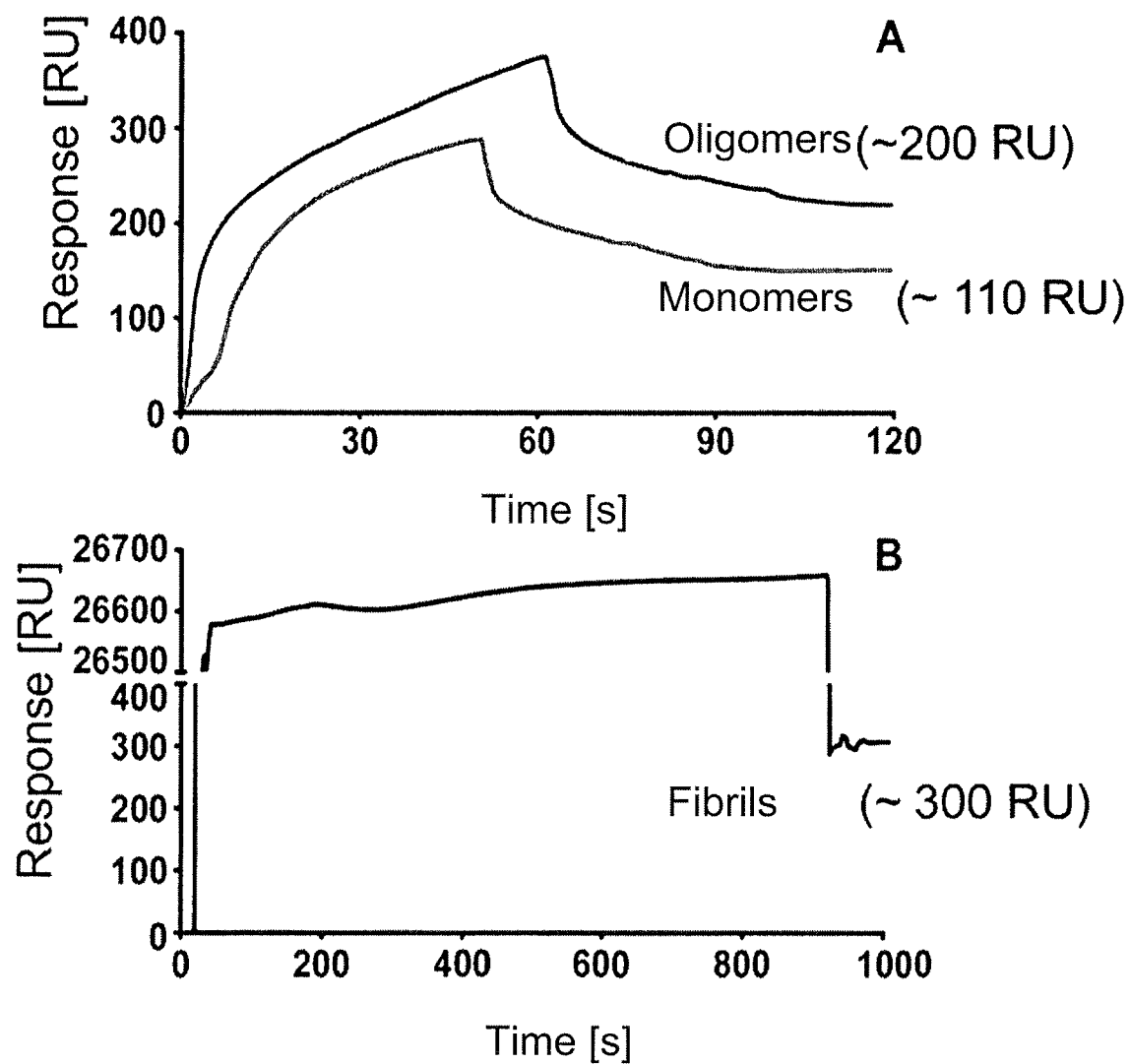
FIG. 2 shows results for the immobilization of monomeric, oligomeric and fibrillar Aβ(1-42) forms on streptavidin-loaded SPR sensor surfaces.

In FIG. 2, the response units (RU) during the immobilization injection are plotted on the Y-axis against the time in seconds on the X-axis. FIG. 2 shows in the respective sensorgrams the response units (RU) obtained during the immobilization injection. That is to say that the Aβ 1-42 molecules are incubated on the streptavidin-loaded chip. In the immobilization reactions shown here, ~110 RU monomers, ~200 RU oligomers and ~300 RU fibrils were immobilized and, at the end of the immobilization reaction, a stable baseline is obtained. This shows that the various forms can be successfully immobilized by means of the biotin-streptavidin interaction and, due to the fact that a stable baseline is achieved, the surfaces can now be used for interaction studies.

Figure 3:
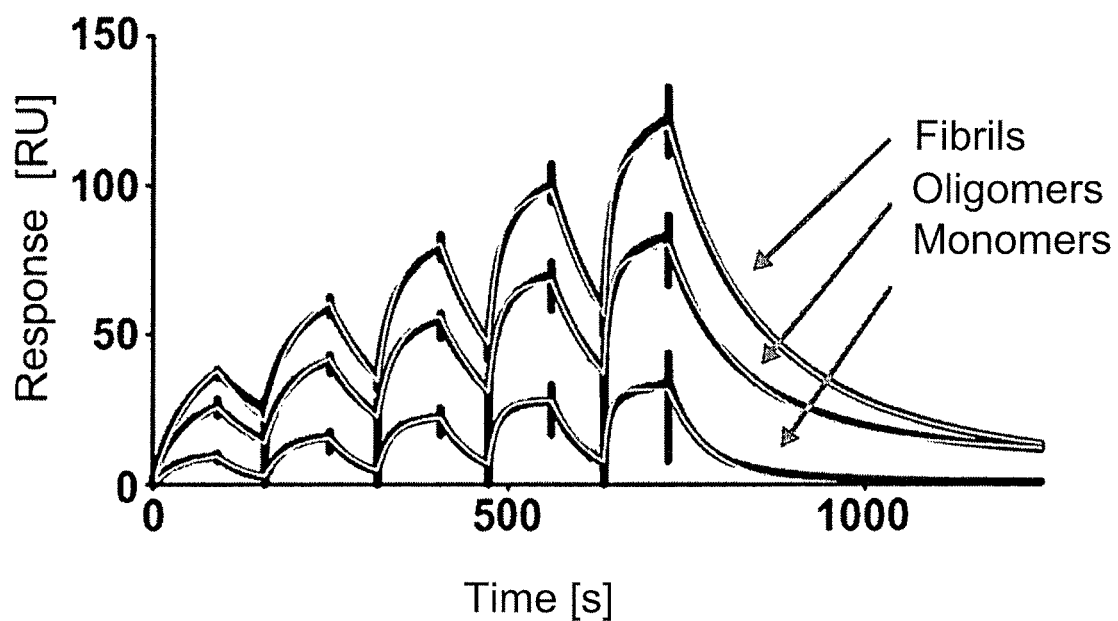
FIG. 3 shows sensorgrams obtained using scFv-IC16 and various Aβ(1-42) conformers.

FIG. 3 shows sensorgrams which were obtained by injecting the single-chain variable fragment (scFv)IC16 in the concentrations 5, 2.5, 1.25, 0.625, 0.3125 μM over sensor surfaces containing immobilized Aβ(1-42) monomers, oligomers and fibrils. The monomers are biotinylated C-terminally, unlike the oligomers and fibrils (N-terminally). The response units (Y-axis) were plotted against the time in seconds (X-axis), wherein the black curves represent the double-referenced experimental data and the gray superposed curves represent the fits. For characterizing the scFv-IC16, therefore, measurements using biotinylated Aβ(1-42) are possible; C-terminally biotinylated Aβ(1-42) was used here. For fitting to monomers, a 1:1 Langmuir binding model was used and oligomers and fibrils were fitted to a heterogeneous binding model which takes account of two different binding sites on the sensor surface. It can clearly be seen that the fits coincide very well with the experimental data. This is direct evidence of the successful immobilization of the various forms and the respectively homogeneous surface. At the same time, this indicates that the determined kinetic parameters for the respective interactions of scFv-IC16 on various forms are based on a robust characterization.

The following overview, in table form, shows the kinetic parameters obtained for Aβ(1-42) monomers, oligomers and fibrils from FIG. 3. $k_a$ represents the association rate, $k_d$ the dissociation rate, $K_D$ the dissociation constant and $R_{max}$ the maximum achievable measurement signal of the antibody fragment scFv-IC16 at the respective binding site of the conformer in Response Units.

|  | Monomers | Monomers[‡] | Oligomers[‡] | Fibrils[‡] |
|---|---|---|---|---|
| $k_{a1}$[a] | $2.27*10^4$ | $2.16*10^4$ | $2.66*10^4$ | $2.96*10^4$ |
| $k_{d1}$[b] | $1.74*10^{-2}$ | $2.03*10^{-2}$ | $0.98*10^{-2}$ | $0.92*10^{-2}$ |
| $K_{D1}$[c] | $7.69*10^{-7}$ | $9.36*10^{-7}$ | $3.70*10^{-7}$ | $3.12*10^{-7}$ |
| $k_{a2}$[a] | — | $4.80*10^4$ | $1.03*10^2$ | $4.54*10^2$ |
| $k_{d2}$[b] | — | $4.78*10^{-9}$ | $5.76*10^{-4}$ | $1.93*10^{-3}$ |
| $k_{D2}$[c] | — | $9.90*10^{-14}$ | $5.60*10^{-6}$ | $4.26*10^{-6}$ |
| $X^2$ | 4.1 | 2.4 | 3.0 | 1.2 |
| $R_{max1}$[d] | 36.6 | 36.2 | 69.1 | 89.3 |
| $R_{max2}$[d] | — | 1.6 | 206.1 | 143.1 |

[‡]fitted to a heterogeneous binding model
[a]$M^{-1}s^{-1}$
[b]$s^{-1}$
[c]M
[d]RU The index a1 and d1 refer respectively to the association and dissociation rate of the antibody fragment scFv-IC16 on the respective exposed epitope of the conformer. The index a2 and d2, on the other hand, refer respectively to the association and dissociation rate of the antibody fragment scFv-IC16 on discontinuous epitopes of the respective conformer. Analogously, the indices D1 and D2 refer to the dissociation constants on the continuous and discontinuous epitope.

Substance to Be Tested:

D7 htrfeyyvyhms, according to SEQ ID NO: 1

Figure 4:
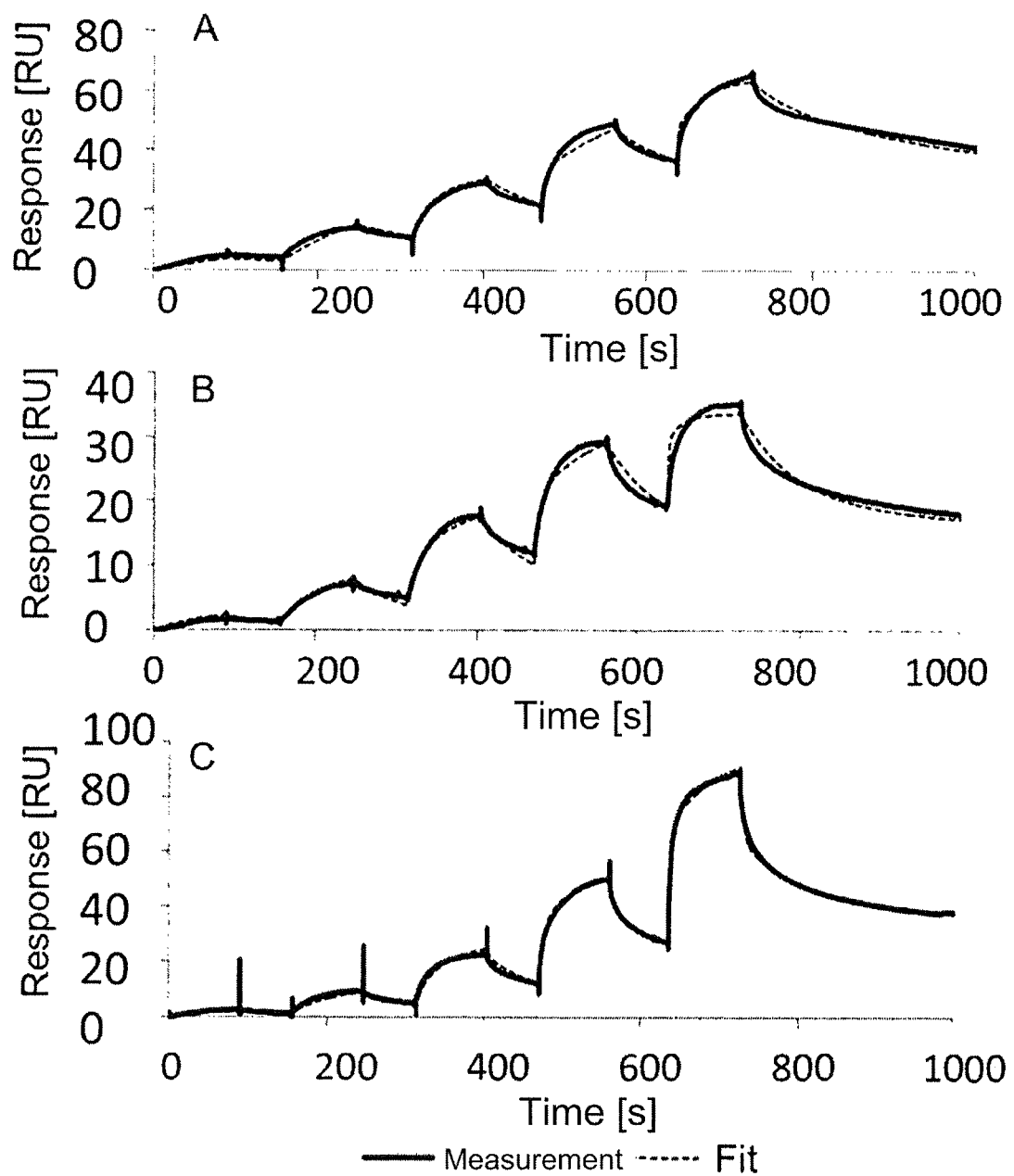
FIG. 4 shows sensorgrams obtained using the peptide D7 and various Aβ(1-42) conformers, that is to say after binding to Aβ(1-42) monomers (A), oligomers (B) and fibrils (C).

The D-enantiomeric peptide D7 was identified by a mirror image phase display selection and analyzed using the method described above with regard to the binding properties, by way of example as a substance to be tested. In a manner differing from the measurement data in FIG. 3, in this case, all the different Aβ(1-42) conformers (monomers, oligomers and fibrils) were prepared by means of density gradient centrifugation and immobilized in various quantities on the sensor surface. In the case of the monomers, 1423 RU were immobilized, in the case of the oligomers 1356 RU, and in the case of the fibrils 1324 RU. The binding data obtained for the kinetic measurements using peptide D7 are shown in FIG. 4. As above in FIG. 3, the measurement was carried out using the single-cycle kinetics method and the response obtained in Response Units is plotted on the Y-axis against the time in seconds on the X-axis. The continuous black line corresponds to the experimental data of the injections of 12.5, 3.13, 0.781, 0.195, 0.0488 μM of D7, starting with the lowest concentration and ending with the highest concentration. It can very clearly be seen here that the method described above is suitable for analyzing a substance to be tested D7 with regard to the properties of binding to various Aβ(1-42) conformers. In addition, this use example serves as evidence that monomers and oligomers, after density gradient centrifugation, can also be immobilized in a manner identical to the fibrils and are subsequently available for binding studies.

The following overview in table form shows the kinetic parameters obtained for Aβ(1-42) monomers, oligomers and fibrils from FIG. 4. $k_a$ represents the association rate, $k_d$ the dissociation rate, $K_D$ the dissociation constant and $R_{max}$ the maximum achievable measurement signal of the peptide D7 at the respective binding site of the conformer in Response Units. The sensorgram for monomeric and oligomeric Aβ(1-42) conformers was fitted to a heterogeneous binding model which takes account of two different binding sites. In the case of the Aβ(1-42) fibrils, a binding model with three different binding sites was taken into account. The indices a1, a2, a3, d1, d2, d3, D1, D2, D3, max1, max2, max3 indicate to which of the discovered sub-reactions the parameters belong.

TABLE 2

Kinetics of Binding between D7 and Aβ
1-42 Monomers, Oligomers and Fibrils

|  | Monomers[‡] | Oligomers[‡] | Fibrils[‡] |
|---|---|---|---|
| $k_{a1}$[a] | 2416 | 4521 | $1.82*10^4$ |
| $k_{d1}$[b] | $3.64*10^{-4}$ | $4.02*10^{-4}$ | 0.2618 |
| $K_{D1}$[c] | $1.51*10^{-7}$ | $8.88*10^{-8}$ | $1.44*10^{-5}$ |
| $k_{a2}$[a] | $1.00*10^5$ | $6.62*10^4$ | 1318 |
| $k_{d2}$[b] | 0.009276 | 0.01527 | $1.93*10^{-4}$ |
| $k_{D2}$[c] | $9.26*10^{-8}$ | $2.31*10^{-7}$ | $1.47*10^{-7}$ |
| $k_{a3}$[a] | — | — | $3.23*10^4$ |
| $k_{d3}$[b] | — | — | 0.0125 |
| $K_{D3}$[c] | — | — | $3.88*10^{-7}$ |
| $X^2$ | 1.32 | 0.5 | 0.62 |
| $R_{max1}$[d] | 37.35 | 19.24 | 57.27 |
| $R_{max2}$[d] | 27.5 | 14.74 | 45.94 |
| $R_{max3}$[d] | — | — | 25.79 |

The method is applied again. After the dissociation of D7 from the Aβ conformer, the surface of the biosensor is again checked using the aggregate quality control probe with regard to the kinetic and/or thermodynamic parameters from the measurement signal and conclusions are drawn about the quality of the surface of the sensor. The method according to the invention therefore ensures that only surfaces of biosensors of sufficiently good quality are used for further substances to be tested.

As a result, advantageously the consumption is reduced and a consistently high quality of the sensor is ensured for subsequent studies.

The invention claimed is:

1. A method for the quantitative characterization of substances with regard to their properties of binding to amyloid-β (Aβ) conformers, comprising the steps of:
   a) preparing in a sample comprising Aβ and N-terminally biotinylated Aβ, and incubating the sample so that various conformers of Aβ are present in the sample though aggregation;
   b) fractionating the sample comprising various Aβ conformers by gradient centrifugation to fractionate and separate the various Aβ conformers;
   c) immobilizing a biotinylated Aβ conformer of a desired fraction, which Aβ conformer is non-monomeric, on the surface of a substrate having high affinity for biotin;
   d) adding an aggregate control probe to the immobilized biotinylated Aβ conformer;
   e) determining kinetic and/or thermodynamic parameters of any binding to the Aβ conformer, and obtaining measurement signal; and
   f) deriving the binding behavior of the aggregate quality control probe to the desired Aβ conformer from the measurement signal, so as to thereby check the quality of the immobilized aggregates;
   wherein a ratio of N-terminally biotinylated to non-biotinylated molecules in a mixture used to produce the sample in step a) is less than or equal to 1:10 to 1:40 or wherein a ratio of N-terminally biotinylated to non-biotinylated molecules in a mixture used to produce the sample in step a) is 1:100.

2. The method according to claim 1, further comprising a step of preparing a sample comprising Aβ and N-terminally biotinylated Aβ or comprising exclusively N-terminally biotinylated Aβ, and incubating said sample so that various conformers of Aβ are present in the sample through aggregation.

3. The method according to claim 1, wherein the sample including Aβ conformers in step a) was obtained from cell culture or by removal from a body.

4. The method according to claim 1, wherein a ratio of N-terminally biotinylated to non-biotinylated molecules in a mixture used to produce the sample in step a) is 1:10 or 1:40 or 1:100.

5. The method according to claim 1, wherein the aggregate quality control probe is antibody fragment scFv-IC16.

6. The method according to claim 1, comprising carrying out surface plasmon resonance or biolayer interferometry to determine the kinetic and/or thermodynamic parameters.

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: D7 peptide D-enantiomeric

<400> SEQUENCE: 1

His Thr Arg Phe Glu Tyr Tyr Val Tyr His Met Ser
1               5                   10

7. The method according to claim 1, wherein a ratio of N-terminally biotinylated to non-biotinylated molecules in a mixture used to produce the sample in step a) is less than or equal to 1:10 to 1:40.

8. The method according to claim 1, wherein the aggregate quality control probe dissociates from Aβ.

9. The method according to claim 8, wherein a substance to be tested is added to the immobilized conformer and the binding behavior of the substance to be tested to the desired Aβ conformer is derived from the measurement signal by determining the kinetic and/or thermodynamic parameters.

10. The method according to claim 9, wherein the substance to be tested is a peptide D7 having the sequence of SEQ ID No. 1.

11. The method according to claim 9, wherein the substance to be tested dissociates from the Aβ conformer.

12. The method according to claim 11, wherein after the substance to be tested dissociates from the Aβ conformer, the aggregate quality control probe is again added to the conformer and the surface of the substrate is checked with regard to the quality for further binding studies.

* * * * *